United States Patent
Wu et al.

(10) Patent No.: US 8,148,113 B2
(45) Date of Patent: Apr. 3, 2012

(54) METHOD FOR PRODUCING GLUCOSAMINE BY CULTURING MICROORGANISM WITH LOW-COST MEDIUM

(75) Inventors: Ho-Shing Wu, Taoyuan County (TW); Yu-Fen Chang, Taoyuan County (TW); Yu-Chiao Wei, Taoyuan County (TW)

(73) Assignee: Yuan Ze University, Taoyuan County (TW)

( * ) Notice: Subject to any disclaimer, the term of this patent is extended or adjusted under 35 U.S.C. 154(b) by 284 days.

(21) Appl. No.: 12/407,171

(22) Filed: Mar. 19, 2009

(65) Prior Publication Data

US 2010/0240105 A1      Sep. 23, 2010

(51) Int. Cl.
    *C12P 19/26*   (2006.01)
(52) U.S. Cl. .................... 435/84; 435/128; 435/171
(58) Field of Classification Search .............. None
    See application file for complete search history.

(56) References Cited

OTHER PUBLICATIONS

Hsieh et al., Biotechnol. Prog., 2007, vol. 23, p. 1009-1016.*
Sánchez-Marroquin et al., Applied Microbiology, 1970, vol. 20, No. 6, p. 888-892.*
Metabolic Engineering for Production of Glucosamine and N-Acetylglucosamine, Deng, et al., Metabolic Engineering 7 (3) 201-214 2005.
Determination and Kinetics of Producing Glucosamine Using Fungi, Hsieh, et al., Biotechnol. Prog., 23, 1009-1016 2007.

* cited by examiner

*Primary Examiner* — Kade Ariani
(74) *Attorney, Agent, or Firm* — WPAT, P.C.; Anthony King

(57) ABSTRACT

A method for producing glucosamine with microorganism comprises of fermenting with a microorganism selected from the group consisting of *Monascus pilosus* and *Aspergillus* sp. in a novel low-cost medium, thereby enable it to produce glucosamine; wherein said medium is consisted of commercial Taiwan sugar, soy beam, rice bran and the like; wherein suitable condition for the fermentation is: 150~300 rpm, pH 4~pH 8, and 24° C.~37° C.; wherein, after fermentation culturing, the fermentation liquor is filtered with suction to recover said microorganism biomass, said microorganism biomass is then subjected to steps of cell disruption, hydrochloric acid reaction, neutralization reaction and filtration, to obtain glucosamine produced by the microorganism.

9 Claims, No Drawings

METHOD FOR PRODUCING GLUCOSAMINE BY CULTURING MICROORGANISM WITH LOW-COST MEDIUM

BACKGROUND OF THE INVENTION

1. Field of the Invention

The invention relates to a method for producing glucosamine by culturing microorganism with a novel low-cost medium.

2. Description of the Prior Art

Glucosamine is one of the constitutional ingredients for articular cartilage, which can provide nutrition for articular tissue, enhance the ability of synovial fluid for recovering lubricating function, promote the regeneration of retrograded joints, and hence effectively reduce the pain generated from bone friction, as well as prevent the aggravation of arthritis condition. Glucosamine can be synthesized by human body itself. However, as age increased, the synthesis speed for glucosamine in the human body is slower than the decomposition speed of glucosamine, and consequently, the body and joints tend to be in short of glucosamine, and further, the metabolism of cells in joints may be affected.

The features of glucosamine include (1) stimulating the regeneration of chondroblast, promoting metabolism thereof, supplying nutrition for bone, reducing inflammation, and vanishing paint; (2) protecting cartilage cells from damage by drugs and external force, and preventing degeneration of joint; (3) increasing the amount of synovial fluid and viscosity thereof, enhancing the lubrication effect of the joint, and improving the function of the joint; (4) ameliorating sore waist and backache. In Europe, glucosamine has been used widely in treating osteo-arthritis. Once administrated, glucosamine can be absorbed fast, delivered to and used by various tissues in the body. The rate acute toxicity assay and microorganism mutagenicity study had shown that glucosamine is a safe and nontoxic health product, and supplement of glucosamine can prevent arthritis.

Glucosamine may be obtained naturally by extracting from chitin in carapace of marine shrimp and crab, as well as artificially by chemical synthesis. At present, industrial production of glucosamine is still carried out by hydrolyzing the carapace of shrimp and crab in hydrochloric acid solution. A conventional method for producing glucosamine comprises of hydrolyzing chitin with acid or enzymes. However, shrimp and crab carapaces obtained from different sources may affect the purity of glucosamine. In addition, glucosamine produced form contaminated shrimp and crab carapaces may be toxic. Furthermore, before hydrolyzing the shrimp and crab carapaces, rinsing of these carapaces is necessary and takes a lot of time and work to prevent notorious stinks. Moreover, glucosamine is not the only one product produced during the process of hydrolyzing the carapaces. Additional purification steps are required in order to isolate glucosamine and other by-products. In the consideration of reducing those tedious pre-treatment steps and diminishing allergic side effect sequela after taking up in the human body, this invention adopts microorganism producing approach instead of a conventional chemical method.

In addition to the above-described hydrolysis method, two methods for producing glucosamine from microorganism are currently used. One of the methods consists of decomposing chitin by means of intracellular and extracellular enzymes of fungus, while the other method consists of converting primary metabolism medium for microorganism into the secondary metabolism medium, for producing glucosamine from the medium.

The study of Deng et al in 2005 pointed out that currently, gene transfer technique had been used to produce glucosamine-producing Escherichia coli. Unfortunately, since the regulatory mechanism involved was too complicated, the detectable amount of glucosamine in the medium for E. coli became extremely low, only several milligram per liter. E. coli produced by gene transfer technology could increase the yield of amino-sugars. Said gene transfer strategy involved the promotion of genes associated with the function and catabolism of glucosamine, as well as the overexpression of the glucosamine synthase gene. Said method could increase up to 15-times of the glucosamine yield, but its titer still remained at the level of milligram. Feedback inhibition of glucosamine synthase had been identified to be a critical factor for applying said method. Further, screening of enzymes might increase the production of glucosamine, and could increase its titer to the level of several grams. Unfortunately, fast degradation of glucosamine in host cell, inhibition effect of glucosamine and degradation product thereof might hinder the increase of the glucosamine concentration [Deng, Ming-de, K. D. Severson, D. A. Grund, S. L. Wassink, R. P. Burlingame, A. Berry, J. A. Running, C. A. Kunesh, L. Song, T. A. Jerrell and R. A. Rosson, From Conceptto Process: Metabolic Engineering for Production of Glucosamine and N-Acetylglucosamine, *Metabolic Engineering*, 7(3), 201-214 (2005)].

In conventional technique and literature, study aimed at producing glucosamine by a way of secondary metabolites of microorganism is neither much nor comprehensive, and only following few fungi have been mentioned to contain glucosamine in their secondary metabolites:

1. *Monasus*: Most of the attention had been focused on contents monacolin K and GABA, far less on the fact that *Monasus* contained glucosamine. Hsieh et al. pointed out in their study in 2007 that in a medium consisting of 20 g/L rice bran, 25 g/L B-grade white crystal sugar, 15 g/L ammonium chloride, *Monascus pilosus* could produce 0.72 g/dm$^3$ of glucosamine, with its optimal condition as: pH 5, and 30° C. [Hsieh, J. W., H. S. Wu, Y. H. Wei, and S. S. Wang, Determination and kinetics of producing glucosamine using fungi, *Biotechnol. Prog.*, 23, 1009-1016(2007)].

2. *Aspergillus*: *Aspergillus* is a filamentous fungus widely present in nature world. Many *Aspergillus* fungi may produce secondary metabolites harmful to human body. Among them, the most well-known one is aflatoxin produced by *Aspergillus flavus* and *Aspergillus parasiticus*. Aflatoxin had been identified as a carcinogenic substance. Nevertheless, Hsieh et al. had indicated in their study in 2007 that, in a certain medium, *Aspergillus* sp. could produce 3.43 g/dm$^3$ of glucosamine, with optimal condition as: pH 7 and 30° C. [Hsieh, J. W., H. S. Wu, Y. H. Wei, and S. S. Wang, Determination and kinetics of producing glucosamine using fungi, *Biotechnol. Prog.*, 23, 1009-1016(2007)].

In view of the foregoing, conventional methods for producing glucosamine still have many disadvantages, and among the other, the production of glucosamine from microorganism fails to increase greatly as well as the cost of the medium is impossible to cut down. Consequently, conventional methods are not well-designed and require further improvement.

The inventors had learned various disadvantages derived from the above-described conventional methods for producing glucosamine, and devoted to improve and innovate, and finally, after studying intensively for many years, has developed successfully a method for producing glucosamine by culturing microorganism with a low-cost medium.

SUMMARY OF THE INVENTION

One object of the invention is to provide a method for producing glucosamine by culturing microorganism with a low-cost medium. The method comprises of developing a novel low-cost medium for culturing microorganism, and producing glucosamine through fermentation, thereby replaces conventional medium and cuts down the cost of the medium.

Another object of the invention is to provide a method for producing glucosamine by culturing microorganism with a low-cost medium, by first using a manner of shaking-flask culturing, then going through fermentation mode to carry out optimization study for the production of glucosamine; and further fermenting with a fermenter to produce glucosamine, in order to increase the production of glucosamine by microorganism.

The method for producing glucosamine by culturing microorganism with a low-cost medium that can achieve the above-mentioned objects of the invention is a method for producing glucosamine by culturing a suitable microorganism with a medium consisting of Taiwan sugars, soy bean, and rice bran, which comprises fermenting under suitable conditions. A suitable microorganism selected from the group consists of *Monascus pilosus* and *Aspergillus* sp., thereby enabling them to produce glucosamine.

The term "suitable microorganism" means the microorganism can produce glucosamine under appropriate culture condition in this invention.

Said *Monascus pilosus* and *Aspergillus* sp. were commonly used bacterium strain. Also, they were both commercially available. The source of suitable microorganism includes, but not limited to *Monascus pilosus* BCRC31527, with an accession number corresponding to ATCC 22080, and *Aspergillus* sp. BCRC31742, with an accession number corresponding to UPCC 3868. Both of the above-mentioned strains could be purchased from Food Industry Development and Research Institute, Hsin-chu, Taiwan, ROC, ATCC, UPCC, or other suitable commercial company. In one preferred embodiment of the invention, said microorganism is preferably *Aspergillus* sp. BCRC 31742.

In one preferred embodiment of the invention, said microorganism *Monascus pilosus* BCRC 31527 is cultured by fermenting in a RBA liquid medium. Said RBA liquid medium is consisted of 25 g/L rice bran, 25 g/L B-grade white crystal sugar and 15 g/L $NH_4Cl$.

In one preferred embodiment of the invention, said microorganism *Monascus pilosus* BCRC 31527 is fermented under stirring at 150~300 rpm, preferably at 150~250 rpm, and most preferably at 200 rpm. In one preferred embodiment of the invention, said microorganism is fermented at pH 4~pH 6, preferably at pH 4.5~pH 5.5, and most preferably at pH 5. In one preferred embodiment of the invention, said microorganism is fermented at 24° C.~37° C., preferably at 28° C.~33° C., and most preferably at 30° C.

In one preferred embodiment of the invention, said microorganism *Aspergillus* sp. BCRC 31742 is cultured separately in WP, WS or WPS liquid media; wherein said WP liquid medium is consisted of suitable concentration of Superior white fine granulated sugar, suitable concentration of Peptone, 0.5 g/L $KH_2PO_4$, 0.5 g/L $MgSO_4.7H_2O$ and 0.1 g/L $CaCl_2.2H_2O$. A preferred WP liquid medium (WP1) is consisted of 25 g/L Superior white fine granulated sugar, 20 g/L Peptone, 0.5 g/L $KH_2PO_4$, 0.5 g/L $MgSO_4.7H_2O$ and 0.1 g/L $CaCl_2.2H_2O$. The most preferably WP liquid medium (WP2) is consisted of 33.9 g/L Superior white fine granulated sugar, 40.6 g/L Peptone, 0.5 g/L $KH_2PO_4$, 0.5 g/L $MgSO_4.7H_2O$ and 0.1 g/L $CaCl_2.2H_2O$; wherein said WS liquid medium is consisted of suitable concentration of Superior white fine granulated sugar, suitable concentration of Soy bean meal or Soy bean, 0.5 g/L $KH_2PO_4$, 0.5 g/L $MgSO_4.7H_2O$ and 0.1 g/L $CaCl_2.2H_2O$. A preferred WS liquid medium (WS1) is consisted of 25 g/L Superior white fine granulated sugar, 50 g/L Soy bean meal, 0.5 g/L $KH_2PO_4$, 0.5 g/L $MgSO_4.7H_2O$ and 0.1 g/L $CaCl_2.2H_2O$. A preferred WS liquid medium (WS2) is consisted of 25 g/L Superior white fine granulated sugar, 20 g/L Soy bean, 0.5 g/L $KH_2PO_4$, 0.5 g/L $MgSO_4.7H_2O$ and 0.1 g/L $CaCl_2.2H_2O$; wherein said WPS liquid medium is consisted of suitable concentration of superior white fine granulated sugar, suitable concentration of Peptone, suitable concentration of Soy bean, 0.5 g/L $KH_2PO_4$, 0.5 g/L $MgSO_4.7H_2O$ and 0.1 g/L $CaCl_2.2H_2O$. A preferred WPS liquid medium (WPS1) is consisted of 25 g/L Superior white fine granulated sugar, 10 g/L Peptone, 23 g/L Soy bean, 0.5 g/L $KH_2PO_4$, 0.5 g/L $MgSO_4.7H_2O$ and 0.1 g/L $CaCl_2.2H_2O$. A preferred WPS liquid medium (WPS2) is consisted of 25 g/L Superior white fine granulated sugar, 40 g/L Peptone, 46 g/L Soy bean, 0.5 g/L $KH_2PO_4$, 0.5 g/L $MgSO_4.7H_2O$ and 0.1 g/L $CaCl_2.2H_2O$.

In one preferred embodiment of the invention, said microorganism *Aspergillus* sp. BCRC 31742 is fermented under stirring at 150~300 rpm, preferably at 150~250 rpm, and most preferably at 200 rpm. Said microorganism is fermented at pH 6~pH 8, preferably at pH 6.5~pH 7.5, and most preferably at pH 7. Said microorganism is fermented at 24° C.~37° C., preferably at 28° C.~33° C., and most preferably at 30° C.

In one preferred embodiment of the invention, after culturing said microorganism by fermentation, the fermentation liquor is filtered with suction to collect biomass of said microorganism, and said biomass of microorganism is subjected to a process comprising steps of cell disruption, acidification with hydrochloric acid, neutralization and filtering, to obtain glucosamine produced by said microorganism; wherein in said acidification step, 1 g of wet biomass is acidified with 6N HCl at 100° C. for 4 hours, to gain a glucosamine concentration approaching an stationary value; and wherein said neutralization reaction is carried out with NaOH to pH 7.

These features and advantages of the present invention will be fully understood and appreciated from the following detailed description and will be illustrated with following non-limiting examples.

DETAILED DESCRIPTION OF THE PREFERRED EMBODIMENT

Example 1

Test Medium

1. Experimental Strains

The invention discloses a method for producing glucosamine by fermenting a non-gene-transferred microorganism with various media. The microorganism used was one of the following: *Monascus pilosus* BCRC31527, with an accession number corresponding to ATCC 22080, and *Aspergillus* sp. BCRC31742, with an accession number corresponding to UPCC 3868. Both of the above-mentioned strains were purchased from Food Industry Development and Research Institute located at Hsin-Chu City in Taiwan, Republic of China.

2. Medium

An appropriate medium was selected based the different characteristics of the above-mentioned two strains for carrying out the production of glucosamine. Media selected for each of the two strains were listed in Table 1.

TABLE 1

Media for various glucosamine-producing strains

| Strain | Medium | Components in medium | Concentration (g/L) |
|---|---|---|---|
| *Monascus pilosus* BCRC31527 | RBA (pH 5) | Rice bran | 25 |
| | | B-grade white crystal sugar | 25 |
| | | $NH_4Cl$ | 15 |

TABLE 1-continued

Media for various glucosamine-producing strains

| Strain | Medium | Components in medium | Concentration (g/L) |
|---|---|---|---|
| *Aspergillus* sp. BCRC31742 | WP1 (pH 7) | Superior white fine Granulated sugar | 25 |
| | | Peptone | 20 |
| | | Basic media | |
| | WP2 (pH 7) | Superior white fine Granulated sugar | 33.9 |
| | | Peptone | 40.6 |
| | | Basic media | |
| | WS1 (pH 7) | Superior white fine Granulated sugar | 25 |
| | | Soy bean meal | 50 |
| | | Basic media | |
| | WS2 (pH 7) | Superior white fine Granulated sugar | 25 |
| | | Soy bean | 20 |
| | | Basic media | |
| *Aspergillus* sp. BCRC31742 | WPS1 (pH 7) | Superior white fine granulated sugar | 25 |
| | | Peptone | 10 |
| | | Soy bean | 23 |
| | | Basic media | |
| | WPS2 (pH 7) | Superior white fine Granulated sugar | 25 |
| | | Peptone | 40 |
| | | Soy bean | 46 |
| | | Basic media | |

Following constituents are commercially available:
RBA: Rice bran (commercial product) + B-grade white crystal sugar (TSC, Taiwan) + Ammonium chloride (NH$_4$Cl, R.D.H., Germany).
WP: Superior white fine granulated sugar + Peptone + Basic media.
WS: Superior white fine granulated sugar + Soy bean (commercial product) + Basic media.
WPS: Superior white fine granulated sugar + Peptone + Soy bean + Basic media.
Basic media: 0.5 g/L KH$_2$PO$_4$ + 0.5 g/L MgSO$_4$•7H$_2$O + 0.1 g/L CaCl$_2$•2H$_2$O.
WS1: Wherein soy bean meal was grounded into powder and 50 g/L of said soy bean meal was added in the medium.
WS2: 20 g/L soy bean (not ground) was added in the medium.
WPS1 and WPS2: Soy bean was milled into powder and suspended homogeneously in distilled water. Most of the dregs were filtered off with filtering cloth, and the filtrate was added in the medium, where its concentration was determined by calculating the weight difference.

Example 2

Shaking-Flask Fermentation Test

Various strains described in Example 1 was activated separately through three region streak plates culturing in Potato Dextrose Agar (PDA) solid medium at 30° C. for 5 days. (Potato Dextrose Agar is consisted of 200 g/L Diced potatoes, 20 g/L Glucose and 15 g/L Agar) Then, single colony was picked up and placed in 200 cm$^3$ sterilized Potato Dextrose Broth (PDB) liquid medium contained in a 250-cm$^3$ shaking-flask, followed by secondary activation through incubating in a thermostatic incubator at 30° C. and 200 rpm for 7 days. (Potato Dextrose Broth is consisted of 20 g/L Diced potatoes and 4 g/L Glucose)

Stains thus-activated was used to inoculate in a suitable medium as shown in Table 1, and the pH of the medium was controlled as follows: pH of the medium used for microorganism *Monascus pilosus* BCRC 31527 was pH 5 and pH of the medium used for microorganism *Aspergillus* sp. BCRC 31742 was pH 7. Thereafter they were incubated at a temperature of 30° C., and 200 rpm for 7 days. Samples were taken and the cell dry weight and yield of glucosamine were determined as follows: the fermentation liquor of *Monascus pilosus* BCRC31527 was poured in a 250-cm$^3$ centrifuge flask and centrifuged at 4° C. and 12,000 rpm for 30 min; the supernatant was decanted, the bacteria pellet was dried in an oven at 100° C., and the cell dry weight was determined (cell dry weight). Further, the pellet was pulverized. 10 cm$^3$ of 6N HCl was added thereto and the mixture was reacted at 100° C. for 24 hours to obtain solution containing glucosamine. Separately, aliquot of fermentation liquor of *Aspergillus* sp. BCRC31742 was dried with suction to obtain a bacteria cake. A sample of the cake was dried in an oven at 100° C., and ratio of wet cell weight to dry cell weight was determined. Furthermore, wet bacteria was disrupted in a cell disrupter, 10 cm$^3$ 6N HCl was added thereto and the mixture was reacted at 100° C. for 4 hours to obtain a solution containing glucosamine. After the solution thus-collected cooled off, 10 cm$^3$ of ultrapure water was added thereto, and the resulted solution was neutralized with NaOH to pH 7, and then a filtrate was collected by filtering with suction. Thereafter, 0.1 cm$^3$ of the filtrate was placed in a test tube. 0.1 cm$^3$ of a solution of 3,5-dinitrobenzonitrile in acetonitrile was added and used as an internal standard, and 0.1 cm$^3$ of 40 mol/m$^3$ solution of 1-naphthyl isothiocyanate in pyridine was added, followed by reacting in a thermostatic water bath at 50° C. for 1 hour. After the reaction, an aliquot of 10 μL was subjected to identification and analysis of glucosamine.

High Performance Liquid Chromatography (HPLC) was used to identify and analyze glucosamine. Analytical conditions for HPLC were as followed:
HPLC pump: Shimadzu LC-10AS
Detector: Shimadzu Model SPD-10Avp UV-VIS index detector
Column: LichroCART RP-18 (5 μm), 250×4 mm I.D.
Mobile phase: Water/Acetonitrile (87/13)
Flow rate: 1.3 cm$^3$/min
UV detecting wavelength: 230 nm The peak area ratio of glucosamine hydrochloride to the internal standard was substituted in the glucosamine hydrochloride calibration curve of the peak area ration of glucosamine hydrochloride to the internal standard to obtain grams of glucosamine by intrapolation method, and converted to glucosamine concentration, glucosamine content, and its yield by converting to carbon source used in the fermentation culturing, and finally, converted against working days to obtain productivity. These results were shown in Table 2.

TABLE 2

Reference (boldface) and glucosamine concentration, glucosamine content, productivity and costs of medium for various strains in shaking-flask culturing

| Strain | medium | Biomass (g/dm$^3$) | Yield (g/g-C) | Glucosamine concentration (g/dm$^3$) | Glucosamine content (g/g-biomass) | Productivity (g/dm$^3$ · h) | Cost of medium (USD/g-glucosamine) | Reference |
|---|---|---|---|---|---|---|---|---|
| Mo-31527 | RBA | 53.4 | 0.09 | 2.33 | 0.05 | 8.5 | 0.42 | |
| Mo | RSA | 17.7 | 0.04 | 0.72 | 0.04 | 4.28 | 3.33 | 1 |
| As-31742 | WP1 | 17.9 | 0.14 | 3.54 | 0.20 | 21.1 | 0.46 | |
| | WP2 | 21.6 | 0.22 | 5.48 | 0.25 | 32.6 | 0.59 | |
| | WS1 | 39.3 | 0.09 | 2.35 | 0.06 | 14.0 | 0.05 | |

TABLE 2-continued

Reference (boldface) and glucosamine concentration, glucosamine content, productivity and costs of medium for various strains in shaking-flask culturing

| Strain | medium | Biomass (g/dm³) | Yield (g/g-C) | Glucosamine concentration (g/dm³) | Glucosamine content (g/g-biomass) | Productivity (g/dm³ · h) | Cost of medium (USD/g-glucosamine) | Reference |
|---|---|---|---|---|---|---|---|---|
|  | WS2 | 22.2 | 0.09 | 2.35 | 0.11 | 14.0 | 0.04 |  |
|  | WPS1 | 24.2 | 0.13 | 3.31 | 0.14 | 19.7 | 0.27 |  |
|  | WPS2 | 21.6 | 0.22 | 5.41 | 0.12 | 32.2 | 0.60 |  |
| As | GP | 18.5 | 0.14 | 3.43 | 0.19 | 20.4 | 0.80 | 1 |

RBA: Rice bran, 0.4 USD/Kg; B-grade white crystal sugar, 0.97 USD/Kg; Ammonium chloride, 55 USD/Kg.
RSA: Rice bran, 0.4 USD/Kg; Sucrose, 88.8 USD/Kg; Ammonium chloride, 55 USD/Kg.
WP1, WP2, WS1, WS2, WPS1, WPS2: Superior white fine granulated sugar, 0.97 USD/Kg; Peptone, 78 USD/Kg; Soy bean, 1.3 USD/Kg; $MgSO_4 \cdot 7H_2O$, 52 USD/Kg; $KH_2PO_4$, 39 USD/Kg; $CaCl_2 \cdot 7H_2O$, 45.5 USD/Kg.
GP: Glucose, 45.8 USD/Kg; Peptone, 78 USD/Kg; $MgSO_4 \cdot 7H_2O$, 52 USD/Kg; $KH_2PO_4$, 39 USD/Kg; $CaCl_2 \cdot 7H_2O$, 45.5 USD/Kg.
Mo-31527: *Monascus pilosus* BCRC 31527;
Mo: *Monascus pilosus* BCRC 31527 (reference 1);
As-31742: *Aspergillus* sp. BCRC 31742;
As: *Aspergillus* sp. BCRC 31742 (reference 1).
Reference 1: Hsieh, J. W., H. S. Wu, Y. H. Wei, and S. S. Wang, Determination and kinetics of producing glucosamine using fungi, *Biotechnol. Prog.*, 23, 1009-1016 (2007)

As shown in Table 2, between two strains used in this example, *Aspergillus* sp. BCRC 31742 cultured in WP2 medium could produce the highest glucosamine concentration (5.48 g/dm³). When it was cultured in WS2 medium, the cost of the medium used to produce glucosamine was the lowest, which is 0.04 USD per gm of glucosamine. Furthermore, as this example culturing *Aspergillus* sp. BCRC 31742 or *Monascus pilosus* BCRC31527 under the condition using the inventive novel medium, *Aspergillus* sp. BCRC 31742 or *Monascus pilosus* BCRC31527 could produce more glucosamine, and the cost of the medium used was far lower compared with those described in reference 1.

Example 3

Fermentation Test in Fermenter

In this example, at first, *Aspergillus* sp. BCRC 31742 described in Example 1 was subjected to secondary activation culturing in accordance with the manner as in Example 2. Then, a fermentation test was carried out in a batchwise stirring fermenter as described below. The 100 cm³ thus-activated *Aspergillus* sp. BCRC 31742 liquor was inoculated in WP1 medium wothin the fermenter, and with a operation volume of 2 dm³, its was subjected to fermentation culture under optimal conditions obtained from shaking-flask experiment: pH 7, a temperature of 30° C., a rotational speed of 200 rpm, and with pure oxygen introduced through external lines to control the dissolved oxygen concentration at 10%.

After recovered from the fermenter, the fermentation liquor was filtered with suction to yield bacterial cake. Next, a sample of the bacteria cake was dried at 100° C., and the ratio of wet cell weight to dry cell weight was determined. Separately, wet cells were disrupted in a cell disrupter. 10 cm³ 6N HCl was added thereto and the mixture was reacted at 100° C. for 4 hours to obtain a liquid containing glucosamine. After the mixture cooled off, 10 cm³ ultrapure water was added, the reaction mixture was neutralized with NaOH to pH 7, and then the reaction mixture was filtered with suction to collect the filtrate. An aliquot of 0.1 cm³ was placed in a test tube. 0.1 cm³ solution of 3,5-dinitrobenzonitrile in acetonitrile was added and used as an internal standard. 0.1 cm³ of 40 mol/m³ solution of 1-naphthyl isothiocyanate in pyridine was added, and the mixture was allowed to react in a constant temperature water bath at 50° C. for 1 hour. After the reaction, an aliquot of 10 μL was subjected to identification and analysis of glucosamin. The same HPLC was carried out to identify and analyze glucosamine. The analytical conditions for HPLC was described as in Example 2.

The peak area ratio of glucosamine hydrochloride to the internal standard was substituted in the glucosamine hydrochloride calibration curve of the peak area ration of glucosamine hydrochloride to the internal standard to obtain grams of glucosamine by intrapolation method, and converted to glucosamine concentration, glucosamine content, and its yield by converting to carbon source used in the fermentation culturing, and finally, converted against working days to obtain productivity. These results were shown in Table 3.

TABLE 3

Reference (boldface) and glucosamine concentration, glucosamine content, yield and productivity obtained in fermenter culturing of *Aspergillus* sp. BCRC 31742 described in example 3.

| Dissolved oxygen | Biomass (g/dm³) | Yield (g/g-carbon source) | Glucosamine concentration (g/dm³) | Glucosamine content (g/g-biomass) | Productivity (g/dm³ · h) | Reference |
|---|---|---|---|---|---|---|
| none | 14.2 | 0.04 | 1.07 | 0.08 | 6.00 |  |
| 5% | 13.7 | 0.05 | 1.25 | 0.09 | 7.44 |  |
| 10% | 14.6 | 0.16 | 3.91 | 0.27 | 23.3 |  |
| 15% | 11.1 | 0.13 | 3.34 | 0.30 | 13.8 |  |
| 20% | 15.2 | 0.14 | 3.51 | 0.23 | 20.9 |  |
| 40% | 15.5 | 0.13 | 3.18 | 0.21 | 18.9 |  |

TABLE 3-continued

Reference (boldface) and glucosamine concentration,
glucosamine content, yield and productivity obtained in fermenter
culturing of Aspergillus sp. BCRC 31742 described in example 3.

| Dissolved oxygen | Biomass (g/dm$^3$) | Yield (g/g-carbon source) | Glucosamine concentration (g/dm$^3$) | Glucosamine content (g/g-biomass) | Productivity (g/dm$^3 \cdot$ h) | Reference |
|---|---|---|---|---|---|---|
| 60% | 13.0 | 0.10 | 2.46 | 0.19 | 14.6 | |
| 60% | 10.0 | 0.09 | 2.31 | 0.23 | 13.7 | 1 |

Reference 1: Hsieh, J. W., H. S. Wu, Y. H. Wei, and S. S. Wang, Determination and kinetics of producing glucosamine using fungi, Biotechnol. Prog., 23, 1009-1016 (2007).

As shown in Table 3, conditions for fermenting *Aspergillus* sp. BCRC 31742 to produce glucosamine described in reference 1 was compared with those used in this Example. When result obtained by culturing *Aspergillus* sp. With GP medium to produce glucosamine as described by Hsieh et al. in 2007 (glucosamine concentration was 2.31 g/dm$^3$) is compared with the result obtained by using the medium described in this example, it is seen that under identical microorganism fermentation conditions, WP medium used in this Example produced a glucosamine concentration (3.91 g/dm$^3$) at a dissolved oxygen of 10% is higher than that reported in the reference.

The method for producing glucosamine by culturing microorganism with a low-cost medium has the following advantages over other conventional methods:

1. The production of glucosamine obtained by the inventive method is higher than that reported in the prior literature.
2. The cost of the medium for producing glucosamine used in the inventive method is far lower than that reported in the prior literature.
3. The analytical method used in the inventive method is easy to operate, has fewer steps, and is simpler compared with the analytical method used in the literature.

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

What is claimed is:

1. A method for producing glucosamine with *Aspergillus* sp. comprising fermenting a liquid medium with an *Aspergillus* sp. under conditions suitable to produce glucosamine, wherein the medium is consisted of 26-40 g/L white fine granulated sugar, 21-41 g/L Peptone, 0.5 g/L KH$_2$PO$_4$, 0.5 g/L MgSO$_4$•7H$_2$O and 0.1 g/L CaCl$_2$•2H$_2$O.

2. A method for producing glucosamine with the *Aspergillus* sp. as recited in claim 1, wherein the liquid medium is consisted of 33.9 g/L white fine granulated sugar, 40.6 g/L Peptone, 0.5 g/L KH$_2$PO$_4$, 0.5 g/L MgSO$_4$.7H$_2$O and 0.1 g/L CaCl$_2$.2H$_2$O.

3. A method for producing glucosamine with microorganism as recited in claim 1, wherein said liquid medium is consisted of 25 g/L white fine granulated sugar, 50 g/L Soy bean meal, 0.5 g/L KH$_2$PO$_4$, 0.5 g/L MgSO$_4$.7H$_2$O and 0.1 g/L CaCl$_2$.2H$_2$O.

4. A method for producing glucosamine with microorganism as recited in claim 1, wherein said liquid medium is consisted of 25 g/L white fine granulated sugar, 20 g/L Soy bean, 0.5 g/L KH$_2$PO$_4$, 0.5 g/L MgSO$_4$.7H$_2$O and 0.1 g/L CaCl$_2$.2H$_2$O.

5. A method for producing glucosamine with microorganism as recited in claim 1, wherein said liquid medium is consisted of 25 g/L white fine granulated sugar, 10 g/L Peptone, 23 g/L Soy bean, 0.5 g/L KH$_2$PO$_4$, 0.5 g/L MgSO$_4$.7H$_2$O and 0.1 g/L CaCl$_2$.2H$_2$O.

6. A method for producing glucosamine with microorganism as recited in claim 1, wherein said liquid medium is consisted of 25 g/L white fine granulated sugar, 40 g/L Peptone, 46 g/L Soy bean, 0.5 g/L KH$_2$PO$_4$, 0.5 g/L MgSO$_4$.7H$_2$O and 0.1 g/L CaCl$_2$.2H$_2$O.

7. A method for producing glucosamine with the microorganism as recited in claim 1, wherein said microorganism is fermented under a condition of pH 6-pH 8.

8. A method for producing glucosamine with microorganism as recited in claim 1, wherein said microorganism is fermented under a condition of pH 6-pH 8.

9. A method for producing glucosamine with microorganism as recited in claim 1, wherein said microorganism is fermented under a condition of pH 6-pH 8.

* * * * *